US012272434B2

(12) United States Patent
Syeda-Mahmood et al.

(10) Patent No.: US 12,272,434 B2
(45) Date of Patent: *Apr. 8, 2025

(54) DEDUPLICATION OF MEDICAL CONCEPTS FROM PATIENT INFORMATION

(71) Applicant: Merative US L.P., Ann Arbor, MI (US)

(72) Inventors: Tanveer F. Syeda-Mahmood, Cupertino, CA (US); Chaitanya Shivade, San Jose, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/221,597

(22) Filed: Jul. 13, 2023

(65) Prior Publication Data

US 2023/0360751 A1   Nov. 9, 2023

Related U.S. Application Data

(63) Continuation of application No. 17/350,441, filed on Jun. 17, 2021, now Pat. No. 11,749,387, which is a (Continued)

(51) Int. Cl.
*G16H 10/60* (2018.01)
*G16H 15/00* (2018.01)
(Continued)

(52) U.S. Cl.
CPC ............. *G16H 10/60* (2018.01); *G16H 15/00* (2018.01); *G16H 50/70* (2018.01); *G16H 70/60* (2018.01)

(58) Field of Classification Search
CPC ........ G16H 10/60; G16H 15/00; G16H 50/70; G16H 70/60
(Continued)

(56) References Cited

U.S. PATENT DOCUMENTS 7,822,598 B2  10/2010  Carus et al.
9,922,385 B2   3/2018  Yegnanarayanan
(Continued)

OTHER PUBLICATIONS

Guidry, Alicia F.; Ontology-Based Data Integration of Open Source Electronic Medical Record and Data Capture Systems; University of Washington. ProQuest Dissertations & Theses, 2013. 3609485. (Year: 2013).*

(Continued)

*Primary Examiner* — Hiep V Nguyen
(74) *Attorney, Agent, or Firm* — Stephen J. Walder, Jr.

(57) ABSTRACT

Mechanisms are provided to implement a patient summary generation engine with deduplication of instances of medical concepts. The patient summary generation engine parses a patient electronic medical record (EMR) to extract a plurality of instances of a medical concept, at least two of which utilize different representations of the medical concept. The patient summary generation engine performs a similarity analysis between each of the instances of a medical concept to thereby calculate, for a plurality of combinations of instances of the medical concept, a similarity metric value. The patient summary generation engine clusters the instances of the medical concept based on the calculated similarity metric values for each combination of instances in the plurality of combinations of instances of the medical concept to thereby generate one or more clusters, and select a representative instance of the medical concept from each cluster in the one or more clusters. The patient summary generation engine generates a summary output of the patient EMR comprising the selected representative instances of the medical concept from each cluster.

20 Claims, 5 Drawing Sheets

Related U.S. Application Data continuation of application No. 16/150,414, filed on Oct. 3, 2018, now Pat. No. 11,081,216.

(51) Int. Cl.
*G16H 50/70* (2018.01)
*G16H 70/60* (2018.01)

(58) Field of Classification Search
USPC .......................................................... 705/3
See application file for complete search history.

(56) References Cited

U.S. PATENT DOCUMENTS

| | | | |
|---|---|---|---|
| 10,331,763 B2 | 6/2019 | Subramanian et al. | |
| 2011/0078145 A1 | 3/2011 | Chung et al. | |
| 2011/0125734 A1 | 5/2011 | Duboue et al. | |
| 2013/0262142 A1 | 10/2013 | Sethumadhavan et al. | |
| 2014/0350961 A1* | 11/2014 | Csurka | G16H 10/60 705/3 |
| 2015/0350961 A1* | 12/2015 | Cho | H04W 8/08 455/436 |
| 2015/0356270 A1 | 12/2015 | Devarakonda et al. | |
| 2015/0370972 A1 | 12/2015 | Chaudhri et al. | |
| 2015/0370979 A1 | 12/2015 | Boloor et al. | |
| 2016/0019299 A1 | 1/2016 | Boloor et al. | |
| 2016/0019356 A1 | 1/2016 | Martin et al. | |
| 2017/0109477 A1 | 4/2017 | Farooq et al. | |
| 2017/0193185 A1* | 7/2017 | Barker | G06F 16/334 |
| 2018/0075192 A1 | 3/2018 | Sethumadhavan et al. | |
| 2019/0163875 A1 | 5/2019 | Allen et al. | |
| 2019/0252047 A1 | 8/2019 | Boloor et al. | |
| 2019/0287660 A1 | 9/2019 | Oliveira et al. | |
| 2019/0362825 A1 | 11/2019 | Haley | |
| 2019/0371475 A1 | 12/2019 | Oliveira et al. | |
| 2020/0111545 A1 | 4/2020 | Syeda-Mahmood et al. | |
| 2021/0313025 A1 | 10/2021 | Syeda-Mahmood et al. | |

OTHER PUBLICATIONS

Banton, Cynthia L ; The impact of multiple master patient index records on the business performance of health care organizations: A qualitative grounded theory study; University of Phoenix. ProQuest Dissertations & Theses, 2014. 3583226. (Year: 2014).*

Cogley, James, "Applying Natural Language Processing to Clinical Information Retrieval", University College of Dublin, Ireland, School of Computer Science and Informatics, ProQuest Dissertations Publishing, 205 Pages, Feb. 2014.

Guidry, Alicia F., "Ontology-Based Data Integration of Open Source Electronic Medical Record and Data Capture Systems", University of Washington, ProQuest Dissertations Publishing, 2013, 3609485, Year: 2013.

High, Rob, "The Era of Cognitive Systems: An Inside Look at IBM Watson and How it Works", IBM Corporation, Redbooks, Dec. 12, 2012, 16 pages.

Yuan, Michael J., "Watson and healthcare, How natural language processing and semantic search could revolutionize clinical decision support", IBM Corporation, IBM developerWorks, http://www.ibm.com/developerworks/industry/library/ind-watson/, Apr. 12, 2011, 14 pages.

* cited by examiner

GI bleed
Other and unspecified hyperlipidemia
Bradycardia
Mitral regurgitation
AORTIC ROOT DILATION (HCC)
Aortic root dilatation (HCC)
Acute gout of right foot
Paroxysmal atrial fibrillation (HCC)
Atrial fibrillation (HCC)
Fall in elderly patient
Chronic kidney disease, stage III (moderate)
Autonomic orthostatic hypotension Hx of amiodarone therapy
UTI (urinary tract infection) due to Enterococcus
Obstructive sleep apnea
Dyspnea
Anemia due to blood loss
Cardiac pacemaker
Aortic stenosis
Orthostatic hypotension
On amiodarone therapy
Diabetic peripheral autonomic neuropathy (HCC)

Coagulopathy (HCC)
Gout
Diabetes mellitus due to underlying condition with renal complication (HCC)
Obesity
UTI (urinary tract infection)
Dyspnea on exertion
Chronic diastolic heart failure (HCC)
Bradycardia, sinus, persistent, severe (HCC)
Hypotension
Hemorrhagic shock (HCC)
Hyperkalemia
Cellulitis
Acute renal failure (ARF) (HCC)

\*\*\* Consolidating \*\*\*
AORTIC ROOT DILATION (HCC)
Aortic root dilatation (HCC)
\*\*\* Consolidating \*\*\*
Paroxysmal atrial fibrillation (HCC)
Atrial fibrillation (HCC)
\*\*\* Consolidating \*\*\*
Autonomic orthostatic hypotension
Orthostatic hypotension
Hypotension
\*\*\* Consolidating \*\*\*
Hx of amiodarone therapy
On amiodarone therapy
\*\*\* Consolidating \*\*\*
Acute gout of right foot
Gout
\*\*\* Consolidating \*\*\*
UTI (urinary tract infection) due to Enterococcus
UTI (urinary tract infection)
\*\*\* Consolidating \*\*\*
Dyspnea
Dyspnea on exertion
\*\*\* Consolidating \*\*\*
Bradycardia
Bradycardia, sinus, persistent, severe (HCC)

*FIG. 1B*

DEDUPLICATION OF MEDICAL CONCEPTS FROM PATIENT INFORMATION

BACKGROUND

The present application relates generally to an improved data processing apparatus and method and more specifically to mechanisms for deduplication of medical concepts from patient information.

Decision-support systems exist in many different industries where human experts require assistance in retrieving and analyzing information. An example that will is a diagnosis system employed in the healthcare industry. Diagnosis systems can be classified into systems that use structured knowledge, systems that use unstructured knowledge, and systems that use clinical decision formulas, rules, trees, or algorithms. The earliest diagnosis systems used structured knowledge or classical, manually constructed knowledge bases. The Internist-I system developed in the 1970s uses disease-finding relations and disease-disease relations. The MYCIN system for diagnosing infectious diseases, also developed in the 1970s, uses structured knowledge in the form of production rules, stating that if certain facts are true, then one can conclude certain other facts with a given certainty factor. DXplain, developed starting in the 1980s, uses structured knowledge similar to that of Internist-I, but adds a hierarchical lexicon of findings.

Iliad, developed starting in the 1990s, adds more sophisticated probabilistic reasoning where each disease has an associated a priori probability of the disease (in the population for which Iliad was designed), and a list of findings along with the fraction of patients with the disease who have the finding (sensitivity), and the fraction of patients without the disease who have the finding (1-specificity).

In 2000, diagnosis systems using unstructured knowledge started to appear. These systems use some structuring of knowledge such as, for example, entities such as findings and disorders being tagged in documents to facilitate retrieval. ISABEL, for example, uses Autonomy information retrieval software and a database of medical textbooks to retrieve appropriate diagnoses given input findings. Autonomy Auminence uses the Autonomy technology to retrieve diagnoses given findings and organizes the diagnoses by body system. First CONSULT allows one to search a large collection of medical books, journals, and guidelines by chief complaints and age group to arrive at possible diagnoses. PEPID DDX is a diagnosis generator based on PEPID's independent clinical content.

Clinical decision rules have been developed for a number of medical disorders, and computer systems have been developed to help practitioners and patients apply these rules. The Acute Cardiac Ischemia Time-Insensitive Predictive Instrument (ACI-TIPI) takes clinical and ECG features as input and produces probability of acute cardiac ischemia as output to assist with triage of patients with chest pain or other symptoms suggestive of acute cardiac ischemia. ACI-TIPI is incorporated into many commercial heart monitors/defibrillators. The CaseWalker system uses a four-item questionnaire to diagnose major depressive disorder. The PKC Advisor provides guidance on 98 patient problems such as abdominal pain and vomiting.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided, in a data processing system comprising a processor and a memory, the memory comprising instructions that are executed by the processor to configure the processor to implement a patient summary generation engine. The method comprises parsing, by the patient summary generation engine, a patient electronic medical record (EMR) to extract a plurality of instances of a medical concept. At least two instances of the medical concept utilize different representations of the medical concept in the patient electronic medical record. The method further comprises performing, by the patient summary generation engine, a similarity analysis between a plurality of combinations of the instances of the medical concept to thereby calculate, for each combination of instances in the plurality of combinations of instances of the medical concept, a similarity metric value. Moreover, the method comprises clustering, by the patient summary generation engine, the instances of the medical concept based on the calculated similarity metric values for each combination in the plurality of combinations of the instances of the medical concept to thereby generate one or more clusters, and selecting, by the patient summary generation engine, a representative instance of the medical concept from each cluster in the one or more clusters. In addition, the method comprises generating, by the patient summary generation engine, a summary output of the patient EMR comprising the selected representative instances of the medical concept from each cluster.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein:

FIG. 1B is an example of a problem list that may be extracted from a patient electronic medical record (EMR) in accordance with one illustrative embodiment;

DETAILED DESCRIPTION

Figure 1A:
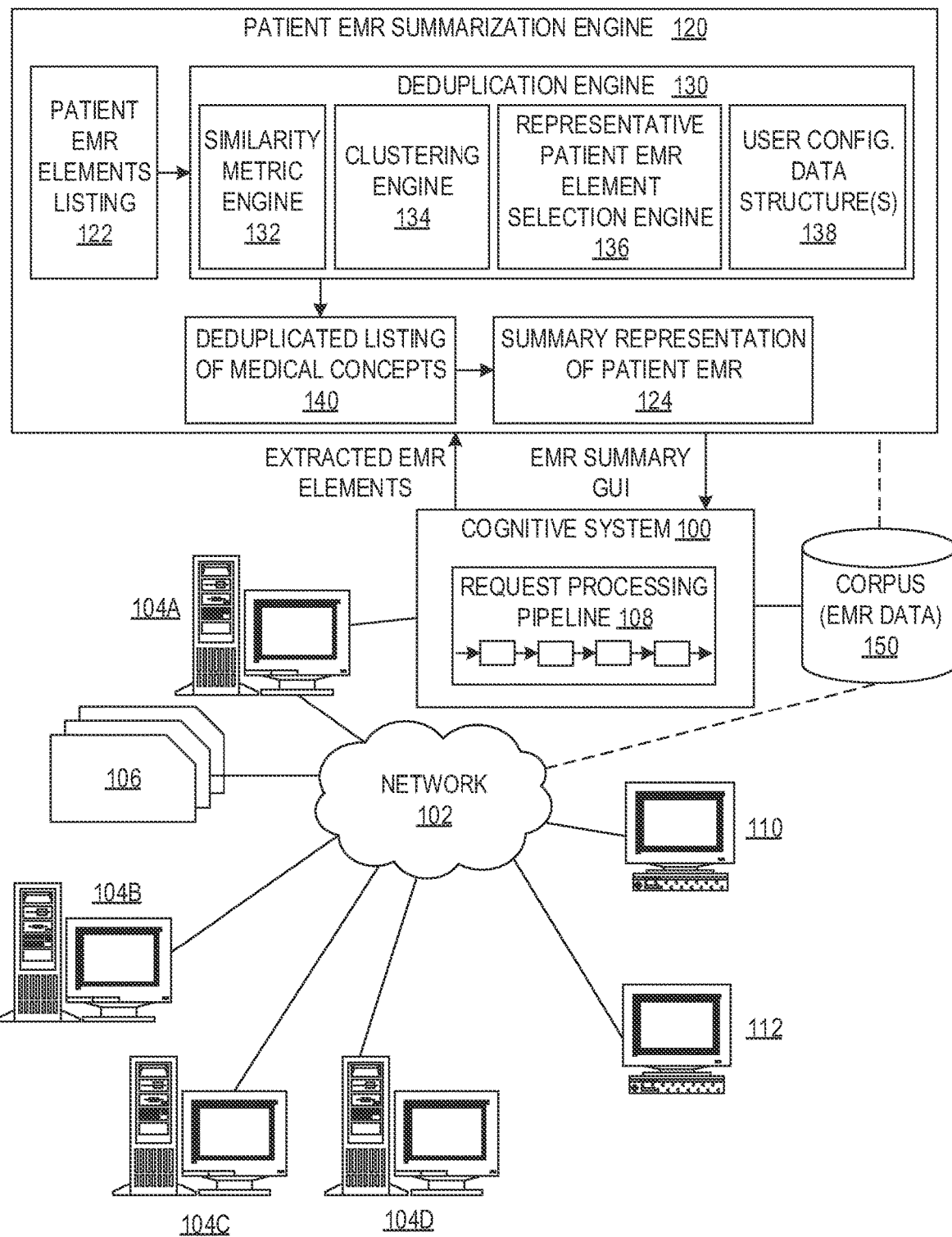
FIG. 1A depicts a schematic diagram of one illustrative embodiment of a cognitive system implementing a request processing pipeline in a computer network.

The strengths of current cognitive systems, such as current medical diagnosis, patient health management, patient treatment recommendation systems, law enforcement investigation systems, and other decision support systems, are that they can provide insights that improve the decision making performed by human beings. For example, in the medical context, such cognitive systems may improve medical practitioners' diagnostic hypotheses, can help medical practitioners avoid missing important diagnoses, and can assist medical practitioners with determining appropriate treatments for specific diseases. However, current systems still suffer from significant drawbacks which should be addressed in order to make such systems more accurate and usable for a variety of applications as well as more representative of the way in which human beings make decisions, such as diagnosing and treating patients.

For example, patient medical records contain a large amount of information about a patient's current and historical medical conditions, diagnoses, and treatments. This is especially true as modern computing systems become more integrated allowing various sources of medical information about patients to contribute to the patient's electronic medical record. For example, electronic medical data from various sources, such as hospitals, clinics, doctor's offices, pharmacies, medical laboratories, and the like, may be integrated into the patient's medical record.

Because of the large amount of information present in a patient's electronic medical record, it is desirable for a medical professional to be able to summarize a patient's medical records so as to obtain a succinct understanding of the patient's medical history, current medical condition, and treatments so that the medical professional can be apprised of the most pertinent information needed to treat the patient without having to sift through a voluminous amount of information to identify the relevant information to the medical professional's intended purpose. However, generating a summary of a patient's medical records that does not contain superfluous information is difficult. For example, the information in a patient's electronic medical record may often include repetitive information which cannot be easily identified due to the various sources of information using different nomenclatures and coding schemes. For example, a patient may take the same medication or undergo the same treatment multiple times over a course of time and each instance may be recorded in the patient information of the patient electronic medical record (EMR), potentially using different names, terms, phrases, medical codes, etc. which may generally refer to the same medical concept but are themselves not exactly the same.

When summarizing the patient EMR, it is not preferred or beneficial to have such repetitious information presented repeatedly in the summary representation of the patient information since the summary is intended to be a compact representation for quick browsing and to provide useful information that is quickly and easily accessible. This will not be the case when the summary representation is populated with repetitions information.

Thus, it would be desirable to be able to remove duplicate information from a summary of a patient EMR. However, it is not a simple matter to remove duplicate information from a patient EMR when generating a summary representation of the patient EMR. Many times, the same information may be identified in different ways by the same or different sources of information. That is, the same medical concept, e.g., disease, symptoms, diagnoses, medications, treatments, etc., may be represented with different terminology, different medical codes, different phrasing in notes input by medical professionals, etc.

Known deduplication mechanisms are limited to searching for the same exact text/phrase in a document in order to remove the duplicate text/phrase. Thus, exact, or substantially similar, text representations are required in order to determine duplicate elements. This is insufficient to address the issues of deduplication of medical concepts in electronic medical records as such known mechanisms will be unlikely to identify the majority of duplications in patient electronic medical records where substantially different representations of the same medical concepts are present within an electronic medical record, e.g., two different medical codes used by two different sources which each represent the same medical concept.

The illustrative embodiments provide mechanisms for performing deduplication of medical concepts in patient electronic medical records when generating a summary representation of the patient electronic medical record. With the illustrative embodiments, the lexical and semantic similarity is combined to identify a set of related phrases in a clinical data phrase list of a clinical category, such as problem lists, diagnosis, medications, symptoms, tests ordered, etc. A similarity metric is utilized to judge the lexical and semantic similarity of candidate phrases, medical codes, terms, etc., and a connected component algorithm is used to consolidate these phrases, terms, codes, etc., into a cluster. A representative element, e.g., phrase, term, code, or the like, is selected from the cluster as a deduplicated element of the relevant medical concept for use in generating a summary representation of a patient's electronic medical record. The resulting summary is more usable by medical personnel and easier to browse, allowing the medical personnel to obtain a necessary information for providing decision support more quickly and efficiently.

With the mechanisms of the illustrative embodiments, a patient EMR is received and parsed to extract all the terms, phrases, medical codes, etc., associated with a particular clinical data category, e.g., problem list, diagnosis, medications, symptoms, tests ordered, etc. For example, the patient EMR may be parsed to extract the problem list of the patient indicating all the medical problems associated with the patient. The terms, phrases, codes, etc., (collectively referred to as patient EMR elements) that are extracted may be determined by using established knowledge bases, ontologies, dictionary data structures, medical coding scheme data structures, and the like, that specify recognizable patient EMR elements. These knowledge bases, which may comprise multiple knowledge resource data structures, may be specific to the particular clinical data category for which the operations of the illustrative embodiments are invoked. Thus, there may be different knowledge bases, or different knowledge resource data structures within a knowledge base, for each of the different supported clinical data categories for which the mechanisms of the illustrative embodiments may be invoked.

Having generated a listing of the patient EMR elements corresponding to the particular clinical data category, for each pairing of patient EMR elements, a similarity metric is utilized to judge the lexical and semantic similarity of the pair of patient EMR elements, where a similarity of "1", for example, indicates that the phrases are lexically and semantically similar, and a similarity metric value less than "1" indicates a relatively lower level of similarity down to a value of "0" indicating no lexical or semantic similarity. The lexical similarity assesses the similarity in the words constituting the phrase denoting the name of the entity. For example, Autonomic orthostatic hypotension and Orthostatic hypotension both share 2 of the 3 names.

In general, lexical similarity needs to take into account spelling errors, missing and spurious words. Ideally, lexical similarity analysis should be tolerant to the word variant formation based on rules of grammar (English, in this case) for tenses, active or passive voices, singular or plural while retaining the semantics. Further, the matching should be robust to a few missing words or presence of extra words. The "longest common subfix" algorithm is one example of a lexical similarity analysis that may be utilized which accommodates some tolerance of word variants. With the longest common subfix algorithm, given two phrases $S=\langle s_1 s_2 \ldots s_K \rangle$ of K words $T=\langle t_1 t_2 \ldots t_N \rangle$ of N words, the longest common subfix is defined as $LCF(S,T)=\langle p_1 p_2 \ldots p_L \rangle$, where L is the largest subset of words from S that found a partial match in T, and $p_i$ is a partial match of a word $s_i \in S$ to a word in T. A word $s_i$ in S is said to partially match a word $t_j$ in T if it shares a maximum length common prefix $p_i$ such that $$\frac{|p_i|}{\max\{|s_i|, |t_j|\}} \geq \tau.$$

If the threshold=1.0, for example, this reduces the algorithm to the case of finding exact matches to words of S.

The prefix in this formulation corresponds to the English grammar rules where many word forms of words share common prefixes. This allows for modeling word variants such as regurgitated, regurgitating, and regurgitation as they all share a sufficiently long prefix 'regurgitat'. This also allows for modeling spelling errors, particularly those that are made in the later portion of a word.

It can be shown that the longest common subfix algorithm obeys the principle of optimality, allowing the best matching subphrase to be found using popular dynamic programming algorithms in time quadratic in the length of the sequences to be matched. For this, an array C[i,j] is maintained to calculate the score of matching a fragment of S up to the i-th word and fragment of T up to the j-th word. The dynamic programming matrix is updated according to the algorithm shown in Tables 2A and 2B below. Here $p_{max}(i,j)$ is the longest prefix of the strings $s,t_j$ and $\delta$ is a mismatch penalty, which controls the separation between matched words and prevents words that are too far apart in a sentence from being associated with the same vocabulary phrase, thus minimizing the effect of incorrect anaphora resolution in a sentence. Using this algorithm, a phrase S is said to be detected within another phrase T $$\frac{|LCF(S, T)|}{|S|} \geq \Gamma$$

if for some threshold $\Gamma$. This also constitutes a lexical similarity measure.

TABLE 2A

LCF(S,T);
C[i, 0] = 0, C[0, j] = 0,
for (1)
for (1
{
;
If C[i−1,j−1] + > C[i−1,j] && C[i−1, j−1]
+ > C[i,j−1]
C[i,j] = C[i−1,j−1] + ;
Else
{
If C[i−1,j] + > C[i,j−1]
C[i,j] = C[i−1,j] − ;
Else
C[i,j] = C[i,j−1] − ;
}
}

TABLE 2B findSmallestForm (word)
{
found = false;
i = word.length( );
prefix = word;
while (!found && i >= 3)
{
prefix = word.substring(0,i);
if ((prefix not in wordMap) || (prefix not
shared in wordMap))
{
i−−; // continue shrinking
}
else
{
found = true;
prefix = word.substring(0, i + 1);
}
}
return prefix;
}

Other measures could be incorporated to enhance the similarity metric, such as the use of abbreviation expansion, or discarding qualitative descriptor (adjectives) while keeping the core finding. For example, an overlap determination may be made to determine how much overlap there is between one patient EMR element and the other patient EMR element in the pairing. For example, if one patient EMR element is the phrase "high blood pressure" and the other is "high BP." In evaluating the two elements, one can see that the elements each utilize the term "high" and that the acronym BP is sometimes utilized to represent blood pressure. Thus, a comparison of the sub-components of the patient EMR element may be made to determine a degree of overlap of the two patient EMR elements and if the degree of overlap meets or exceeds a predetermined threshold, then the two patient EMR elements are considered to be highly similar.

Another approach to determining similarity between the two patient EMR elements is semantic similarity. Here the words in the phrases need not be similar. Instead, English language semantics or clinical knowledge semantics can be used to determine similarity. The semantic relationship captured is of several types such as two different phrases mapping to the same concept identifier (called CUI) in a unified medical language coding system (UMLS). Since this coding system has already defined relationships between concepts, semantic exploration can use equivalent concepts, synonyms, and concepts related by generalization or specialization hierarchy in the ontology to define similarity. The distance between two concepts in the ontology captured through UMLS can be used as a measure of semantic similarity.

That is, an ontology of medical concepts may be defined with ontological nodes corresponding to medical concepts and links or edges between medical concepts indicating related medical concepts, e.g., related diseases, symptoms, patient demographics, medications treatments, etc. Each of the nodes have associated identifiers. Mapping the patient EMR elements to nodes in the ontology provides associated ontology identifiers which may be used to determine a degree of relationship, or connectivity, between the patient EMR elements, if any. That is, a degree of similarity between the ontology ID of one patient EMR element and that ontology ID of another patient EMR element may be determined based on a distance between the nodes in the ontology.

It should be appreciated that these are only examples of methodologies that may be employed to determine similarities between patient EMR elements. Other methodologies may also be used in addition to, or in replacement of, one or more of these methodologies. Moreover, any combination of methodologies may be used to determine the similarity of patient EMR elements corresponding to medical concepts without departing from the spirit and scope of the illustrative embodiments.

Those patient EMR elements that are considered to be highly similar to one another, e.g., based on the similarity metric value and predetermined thresholds, are considered representative of repetitions or duplicate information in the patient EMR. Some context based filtering of patient EMR elements, or portions thereof, may be performed to ignore patient EMR elements, or portions thereof, that do not identify medical concepts or clinical data, i.e. ignore phrases, such as adjectives indicating severity, standard abbreviations such as HCC (history of current complications, which is not actually part of a disease name and should be ignored). For example, one may identify a patient EMR element of "acute pancreatitis", but the term "acute" is not relevant in the context of a problem list, only the "pancreatitis" is important to the identification of a problem list for the patient EMR.

A union-find connected component algorithm may be executed on the highly similar patient EMR elements to consolidate similar patient EMR elements (again, these may be terms, phrases, medical codes, etc.) into a cluster based on the calculated similarity metrics between the pairings. Thus, for example, phrases that are similar to one another from both a lexical and semantic basis may be clustered with each other while other phrases may be present in other clusters or otherwise not included in a cluster. The algorithm ensures that each member of the cluster remains within the bounds of the similarity metric based on both lexical and semantic similarity.

A representative patient EMR element, e.g., a representative phrase, is then selected from each cluster to represent the cluster of duplicate medical concepts in the patient EMR. For example, if the cluster includes phrases such as "high blood pressure", "high BP", and "hypertension", then a representative phrase of "hypertension" may be selected to represent all of these instances of duplicate medical concepts. In general, the core phrase that is maximally overlapping the members of the cluster that also constitutes its own semantic entity as a concept is chosen as the representative element. In the above example, hypertension by itself is a valid concept in UMLS. Various other ranking rules may be employed for selecting a representative patient EMR element, and these ranking rules may be dependent upon the particular clinical data category. The ranking rules may also be user customizable such that the particular ranking rules implemented for selection of a representative patient EMR element is specific to the user, e.g., one user may want to select phrases that represent the most severe instance of a clinical data phrase, while another user may utilize a different ranking rule such as shortest phrase to give the most generalization, a phrase that corresponds to the concept unique identifier (CUI) with the highest node in an ontology traversed, etc. In this way, the patient EMR summaries generated are made user customizable in that the user is presented with representative patient EMR elements that they recognize as most usable to them. A default ranking rule may be utilized to select a representative patient EMR element by analyzing the cluster to identify those patient EMR elements that are closest to the center point of the cluster, as well as analyze the patient EMR elements in the clusters for various characteristics, e.g., parts of speech, and utilize these criteria to select a patient EMR element having a desirable characteristics and which is closest to the center of the cluster.

A summary representation of the patient EMR information may then be generated via a graphical user interface. The summary representation may include the representative patient EMR elements, but with duplicate instances of patient EMR elements corresponding to similar medical concepts having been removed. Thus, rather than having three separate instances of "high blood pressure", "high BP", and "hypertension", the patient EMR summary may simply indicate "hypertension" being associated with the patient. Other characteristics of the instances of the duplicate medical concepts may be associated with the same deduplicated entry in the summary representation. For example, a single instance of "hypertension" may be included in the summary with corresponding characteristics indicating timestamps when the patient was diagnosed with the medical concept, regardless of the particular terms/phrases/codes used to indicate the medical concept. Thus, for example, for "hypertension" there may be a first timestamp associated with the date that the note "high blood pressure" was included in the patient EMR, a second timestamp when "high BP" was noted, and a third timestamp when "hypertension" was noted. Other characteristics may also be included, such as any related clinical values, or the like. This information may be accessible via a "drill-down" mechanisms of the graphical user interface whereby the user may drill down into more detailed information from higher level abstracted views, for example.

The process described above may be performed with regard to a plurality of different clinical data categories. The patient information in the patient EMR for each of these clinical data categories may be deduplicated using the mechanisms of the illustrative embodiments so as to eliminate duplicated instances of the same medical concepts present within the patient EMR data. The resulting deduplicated patient information may together be compiled into the summary representation of the patient EMR data which is more concise and able to be browsed by the medical professional to obtain a quick and clear representation of the medical condition of the patient. The summary representation is presented in a graphical user interface such that the medical professional may be able to access the underlying detailed information corresponding to the summary representation.

Before beginning the discussion of the various aspects of the illustrative embodiments in more detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a", "at least one of", and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," as used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations. It should be appreciated, however, that when a computing device is specifically configured to implement such an engine, or engines, the computing device is not a general purpose computing device simply performing generic computing operations, but instead is a specially configured computing device performing the specific ordered combination of operations set forth in the specific embodiment for achieving a desired result in a specific manner.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As noted above, the present invention provides mechanisms for deduplicating medical concepts present in patient EMR data when generating a summary representation of the patient EMR data. The illustrative embodiments combine semantic and lexical similarity evaluations to generate a similarity metric between patient EMR elements which are then used to cluster the patient EMR elements into clusters representing instances of patient EMR elements are duplicates of the same medical concept. A representative patient EMR element is then selected for each cluster and is included in the patient EMR summary representation. Information corresponding to the various instances of the medical concept may be associated with the single representation of the medical concept in the patient EMR summary representation, e.g., timestamps, clinical data values, etc., such that these instances may be accessible via the graphical user interface when a user drills down into the details associated with the single representative patient EMR element.

Figure 2:
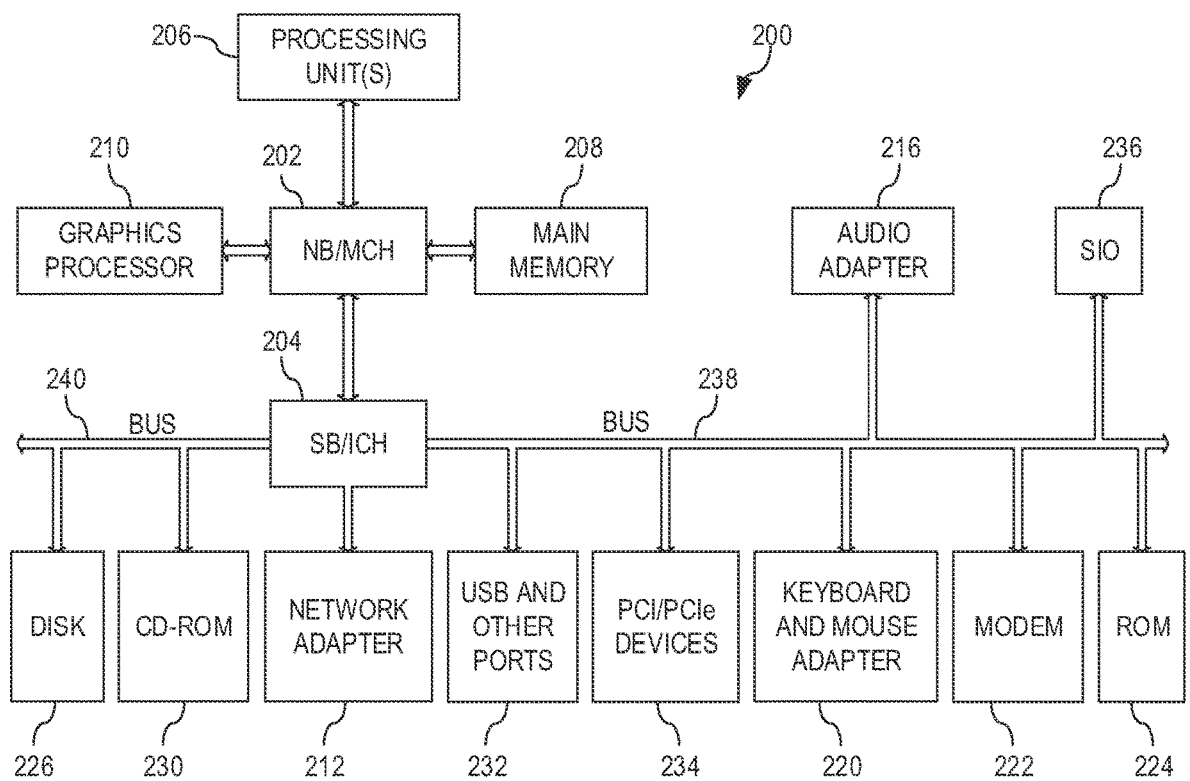
FIG. 2 is a block diagram of an example data processing system in which aspects of the illustrative embodiments are implemented.
Figure 3:
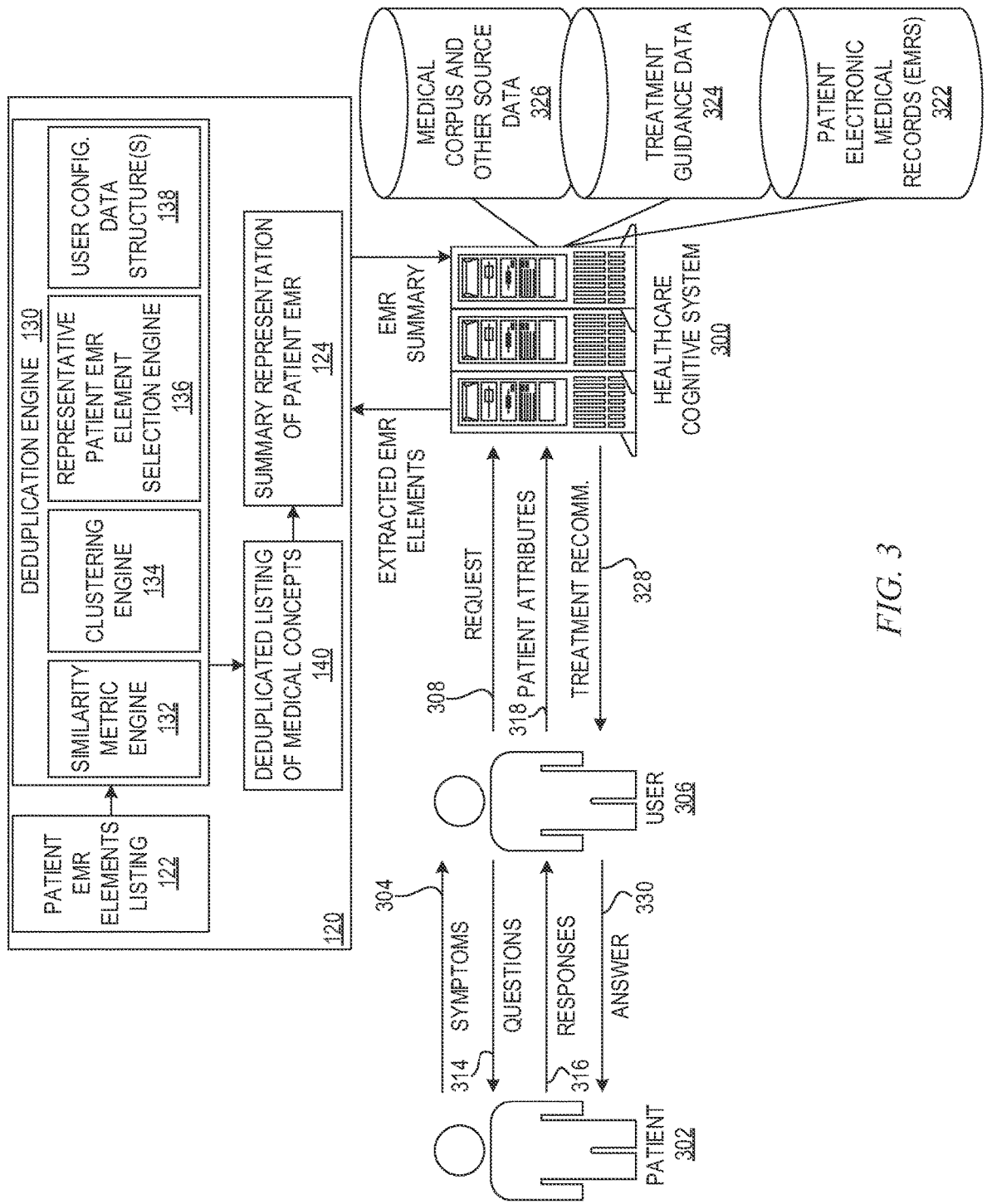
FIG. 3 is an example diagram illustrating an interaction of elements of a healthcare cognitive system in accordance with one illustrative embodiment.

The illustrative embodiments may be utilized in many different types of data processing environments. In order to provide a context for the description of the specific elements and functionality of the illustrative embodiments, FIGS. 1-3 are provided hereafter as example environments in which aspects of the illustrative embodiments may be implemented. It should be appreciated that FIGS. 1-3 are only examples and are not intended to assert or imply any limitation with regard to the environments in which aspects or embodiments of the present invention may be implemented. Many modifications to the depicted environments may be made without departing from the spirit and scope of the present invention.

FIGS. 1-3 are directed to describing an example cognitive system for healthcare applications (also referred to herein as a "healthcare cognitive system") which implements a request processing pipeline, such as a Question Answering (QA) pipeline (also referred to as a Question/Answer pipeline or Question and Answer pipeline) for example, request processing methodology, and request processing computer program product with which the mechanisms of the illustrative embodiments are implemented. These requests may be provided as structure or unstructured request messages, natural language questions, or any other suitable format for requesting an operation to be performed by the healthcare cognitive system. As described in more detail hereafter, the particular healthcare application that is implemented in the cognitive system of the present invention is a healthcare application for patient electronic medical record (EMR) summarization for decision support for a medical professional in which duplicate medical concepts present in the patient EMR are removed from the summarization so as to make the patient EMR summary representation more concise, browsable, and easy to use to obtain an understanding of the patient's pertinent medical history and current medical condition, as well as treatments, medications, and other medical concepts.

It should be appreciated that the healthcare cognitive system, while shown as having a single request processing pipeline in the examples hereafter, may in fact have multiple request processing pipelines. Each request processing pipeline may be separately trained and/or configured to process requests associated with different domains or be configured to perform the same or different analysis on input requests (or questions in implementations using a QA pipeline), depending on the desired implementation. For example, in some cases, a first request processing pipeline may be trained to operate on input requests directed to a providing patient EMR summaries associated with problem lists while another request processing pipeline may be trained to process requests directed to providing patient EMR summaries for medications, treatments, or the like.

Moreover, each request processing pipeline may have their own associated corpus or corpora that they ingest and operate on, e.g., one corpus for medical knowledge documents and/or ontology data structures associated with particular types of problem lists, and another corpus for particular types of treatments, medications, or the like. In some cases, the request processing pipelines may each operate on the same domain of input requests but may have different configurations, e.g., different annotators or differently trained annotators, such that different analysis and potential answers are generated. The healthcare cognitive system may provide additional logic for routing input requests to the appropriate request processing pipeline, such as based on a determined domain of the input request, combining and evaluating final results generated by the processing performed by multiple request processing pipelines, and other control and interaction logic that facilitates the utilization of multiple request processing pipelines.

As noted above, one type of request processing pipeline with which the mechanisms of the illustrative embodiments may be utilized is a Question Answering (QA) pipeline. The description of example embodiments of the present invention hereafter will utilize a QA pipeline as an example of a request processing pipeline that may be augmented to include mechanisms in accordance with one or more illustrative embodiments. It should be appreciated that while the present invention will be described in the context of the cognitive system implementing one or more QA pipelines that operate on an input question, the illustrative embodiments are not limited to such. Rather, the mechanisms of the illustrative embodiments may operate on requests that are not posed as "questions" but are formatted as requests for the cognitive system to perform cognitive operations on a specified set of input data using the associated corpus or corpora and the specific configuration information used to configure the cognitive system. For example, rather than asking a natural language question of "What medical problems are associated with patient P?", the cognitive system may instead receive a request of "generate problem list for patient P," or the like. It should be appreciated that the mechanisms of the QA system pipeline may operate on requests in a similar manner to that of input natural language questions with minor modifications. In fact, in some cases, a request may be converted to a natural language question for processing by the QA system pipelines if desired for the particular implementation.

As an overview, a cognitive system is a specialized computer system, or set of computer systems, configured with hardware and/or software logic (in combination with hardware logic upon which the software executes) to emulate human cognitive functions. These cognitive systems apply human-like characteristics to conveying and manipulating ideas which, when combined with the inherent strengths of digital computing, can solve problems with high accuracy and resilience on a large scale. A cognitive system performs one or more computer-implemented cognitive operations that approximate a human thought process as well as enable people and machines to interact in a more natural manner so as to extend and magnify human expertise and cognition. A cognitive system comprises artificial intelligence logic, such as natural language processing (NLP) based logic, for example, and machine learning logic, which may be provided as specialized hardware, software executed on hardware, or any combination of specialized hardware and software executed on hardware. The logic of the cognitive system implements the cognitive operation(s), examples of which include, but are not limited to, question answering, identification of related concepts within different portions of content in a corpus, intelligent search algorithms, such as Internet web page searches, for example, medical diagnostic and treatment recommendations, and other types of recommendation generation, e.g., items of interest to a particular user, potential new contact recommendations, or the like.

IBM Watson™ is an example of one such cognitive system which can process human readable language and identify inferences between text passages with human-like high accuracy at speeds far faster than human beings and on a larger scale. In general, such cognitive systems are able to perform the following functions:

Navigate the complexities of human language and understanding

Ingest and process vast amounts of structured and unstructured data

Generate and evaluate hypothesis

Weigh and evaluate responses that are based only on relevant evidence

Provide situation-specific advice, insights, and guidance

Improve knowledge and learn with each iteration and interaction through machine learning processes Enable decision making at the point of impact (contextual guidance)

Scale in proportion to the task

Extend and magnify human expertise and cognition

Identify resonating, human-like attributes and traits from natural language

Deduce various language specific or agnostic attributes from natural language

High degree of relevant recollection from data points (images, text, voice) (memorization and recall)

Predict and sense with situational awareness that mimic human cognition based on experiences Answer questions based on natural language and specific evidence In one aspect, cognitive systems provide mechanisms for answering questions posed to these cognitive systems using a Question Answering pipeline or system (QA system) and/or process requests which may or may not be posed as natural language questions. The QA pipeline or system is an artificial intelligence application executing on data processing hardware that answers questions pertaining to a given subject-matter domain presented in natural language. The QA pipeline receives inputs from various sources including input over a network, a corpus of electronic documents or other data, data from a content creator, information from one or more content users, and other such inputs from other possible sources of input. Data storage devices store the corpus of data. A content creator creates content in a document for use as part of a corpus of data with the QA pipeline. The document may include any file, text, article, or source of data for use in the QA system. For example, a QA pipeline accesses a body of knowledge about the domain, or subject matter area, e.g., financial domain, medical domain, legal domain, etc., where the body of knowledge (knowledgebase) can be organized in a variety of configurations, e.g., a structured repository of domain-specific information, such as ontologies, or unstructured data related to the domain, or a collection of natural language documents about the domain.

Content users input questions to cognitive system which implements the QA pipeline. The QA pipeline then answers the input questions using the content in the corpus of data by evaluating documents, sections of documents, portions of data in the corpus, or the like. When a process evaluates a given section of a document for semantic content, the process can use a variety of conventions to query such document from the QA pipeline, e.g., sending the query to the QA pipeline as a well-formed question which is then interpreted by the QA pipeline and a response is provided containing one or more answers to the question. Semantic content is content based on the relation between signifiers, such as words, phrases, signs, and symbols, and what they stand for, their denotation, or connotation. In other words, semantic content is content that interprets an expression, such as by using Natural Language Processing.

The QA pipeline receives an input question, parses the question to extract the major features of the question, uses the extracted features to formulate queries, and then applies those queries to the corpus of data. Based on the application of the queries to the corpus of data, the QA pipeline generates a set of hypotheses, or candidate answers to the input question, by looking across the corpus of data for portions of the corpus of data that have some potential for containing a valuable response to the input question. The QA pipeline then performs deep analysis on the language of the input question and the language used in each of the portions of the corpus of data found during the application of the queries using a variety of reasoning algorithms. There may be hundreds or even thousands of reasoning algorithms applied, each of which performs different analysis, e.g., comparisons, natural language analysis, lexical analysis, or the like, and generates a score. For example, some reasoning algorithms may look at the matching of terms and synonyms within the language of the input question and the found portions of the corpus of data. Other reasoning algorithms may look at temporal or spatial features in the language, while others may evaluate the source of the portion of the corpus of data and evaluate its veracity.

The scores obtained from the various reasoning algorithms indicate the extent to which the potential response is inferred by the input question based on the specific area of focus of that reasoning algorithm. Each resulting score is then weighted against a statistical model. The statistical model captures how well the reasoning algorithm performed at establishing the inference between two similar passages for a particular domain during the training period of the QA pipeline. The statistical model is used to summarize a level of confidence that the QA pipeline has regarding the evidence that the potential response, i.e. candidate answer, is inferred by the question. This process is repeated for each of the candidate answers until the QA pipeline identifies candidate answers that surface as being significantly stronger than others and thus, generates a final answer, or ranked set of answers, for the input question.

FIG. 1A depicts a schematic diagram of one illustrative embodiment of a cognitive system 100 implementing a request processing pipeline 108, which in some embodiments may be a question answering (QA) pipeline, in a computer network 102. For purposes of the present description, it will be assumed that the request processing pipeline 108 is implemented as a QA pipeline that operates on structured and/or unstructured requests in the form of input questions. One example of a question processing operation which may be used in conjunction with the principles described herein is described in U.S. Patent Application Publication No. 2011/0125734, which is herein incorporated by reference in its entirety. The cognitive system 100 is implemented on one or more computing devices 104A-D (comprising one or more processors and one or more memories, and potentially any other computing device elements generally known in the art including buses, storage devices, communication interfaces, and the like) connected to the computer network 102. For purposes of illustration only, FIG. 1A depicts the cognitive system 100 being implemented on computing device 104A only, but as noted above the cognitive system 100 may be distributed across multiple computing devices, such as a plurality of computing devices 104A-D. The network 102 includes multiple computing devices 104A-D, which may operate as server computing devices, and 110-112 which may operate as client computing devices, in communication with each other and with other devices or components via one or more wired and/or wireless data communication links, where each communication link comprises one or more of wires, routers, switches, transmitters, receivers, or the like. In some illustrative embodiments, the cognitive system 100 and network 102 enables question processing and answer generation (QA) functionality for one or more cognitive system users via their respective computing devices 110-112. In other embodiments, the cognitive system 100 and network 102 may provide other types of cognitive operations including, but not limited to, request processing and cognitive response generation which may take many different forms depending upon the desired implementation, e.g., cognitive information retrieval, training/instruction of users, cognitive evaluation of data, or the like. Other embodiments of the cognitive system 100 may be used with components, systems, subsystems, and/or devices other than those that are depicted herein.

The cognitive system 100 is configured to implement a request processing pipeline 108 that receive inputs from various sources. The requests may be posed in the form of a natural language question, natural language request for information, natural language request for the performance of a cognitive operation, or the like. For example, the cognitive system 100 receives input from the network 102, a corpus or corpora of electronic documents 106, cognitive system users, and/or other data and other possible sources of input. In one embodiment, some or all of the inputs to the cognitive system 100 are routed through the network 102. The various computing devices 104A-D on the network 102 include access points for content creators and cognitive system users. Some of the computing devices 104A-D include devices for a database storing the corpus or corpora of data 106 (which is shown as a separate entity in FIG. 1 for illustrative purposes only). Portions of the corpus or corpora of data 106 may also be provided on one or more other network attached storage devices, in one or more databases, or other computing devices not explicitly shown in FIG. 1A. The network 102 includes local network connections and remote connections in various embodiments, such that the cognitive system 100 may operate in environments of any size, including local and global, e.g., the Internet.

In one embodiment, the content creator creates content in a document of the corpus or corpora of data 106 for use as part of a corpus of data with the cognitive system 100. The document includes any file, text, article, or source of data for use in the cognitive system 100. Cognitive system users access the cognitive system 100 via a network connection or an Internet connection to the network 102, and input questions/requests to the cognitive system 100 that are answered/processed based on the content in the corpus or corpora of data 106. In one embodiment, the questions/requests are formed using natural language. The cognitive system 100 parses and interprets the question/request via a pipeline 108, and provides a response to the cognitive system user, e.g., cognitive system user 110, containing one or more answers to the question posed, response to the request, results of processing the request, or the like. In some embodiments, the cognitive system 100 provides a response to users in a ranked list of candidate answers/responses while in other illustrative embodiments, the cognitive system 100 provides a single final answer/response or a combination of a final answer/response and ranked listing of other candidate answers/responses.

The cognitive system 100 implements the pipeline 108 which comprises a plurality of stages for processing an input question/request based on information obtained from the corpus or corpora of data 106. The pipeline 108 generates answers/responses for the input question or request based on the processing of the input question/request and the corpus or corpora of data 106.

In some illustrative embodiments, the cognitive system 100 may be the IBM Watson™ cognitive system available from International Business Machines Corporation of Armonk, New York, which is augmented with the mechanisms of the illustrative embodiments described hereafter. As outlined previously, a pipeline of the IBM Watson™ cognitive system receives an input question or request which it then parses to extract the major features of the question/request, which in turn are then used to formulate queries that are applied to the corpus or corpora of data 106. Based on the application of the queries to the corpus or corpora of data 106, a set of hypotheses, or candidate answers/responses to the input question/request, are generated by looking across the corpus or corpora of data 106 for portions of the corpus or corpora of data 106 (hereafter referred to simply as the corpus 106) that have some potential for containing a valuable response to the input question/response (hereafter assumed to be an input question). The pipeline 108 of the IBM Watson™ cognitive system then performs deep analysis on the language of the input question and the language used in each of the portions of the corpus 106 found during the application of the queries using a variety of reasoning algorithms.

The scores obtained from the various reasoning algorithms are then weighted against a statistical model that summarizes a level of confidence that the pipeline 108 of the IBM Watson™ cognitive system 100, in this example, has regarding the evidence that the potential candidate answer is inferred by the question. This process is be repeated for each of the candidate answers to generate ranked listing of candidate answers which may then be presented to the user that submitted the input question, e.g., a user of client computing device 110, or from which a final answer is selected and presented to the user. More information about the pipeline 108 of the IBM Watson™ cognitive system 100 may be obtained, for example, from the IBM Corporation website, IBM Redbooks, and the like. For example, information about the pipeline of the IBM Watson™ cognitive system can be found in Yuan et al., "Watson™ and Healthcare," IBM developerWorks, 2011 and "The Era of Cognitive Systems: An Inside Look at IBM Watson™ and How it Works" by Rob High, IBM Redbooks, 2012.

As noted above, while the input to the cognitive system 100 from a client device may be posed in the form of a natural language question, the illustrative embodiments are not limited to such. Rather, the input question may in fact be formatted or structured as any suitable type of request which may be parsed and analyzed using structured and/or unstructured input analysis, including but not limited to the natural language parsing and analysis mechanisms of a cognitive system such as IBM Watson™, to determine the basis upon which to perform cognitive analysis and providing a result of the cognitive analysis. In the case of a healthcare based cognitive system, this analysis may involve processing patient medical records, medical guidance documentation from one or more corpora, and the like, to provide a healthcare oriented cognitive system result.

In the context of the present invention, cognitive system 100 may provide a cognitive functionality for assisting with healthcare based operations. For example, depending upon the particular implementation, the healthcare based operations may comprise patient diagnostics, medical treatment recommendation systems, medical practice management systems, personal patient care plan generation and monitoring, patient electronic medical record (EMR) evaluation for various purposes, such as for identifying patients that are suitable for a medical trial or a particular type of medical treatment, or the like. Thus, the cognitive system 100 may be a healthcare cognitive system 100 that operates in the medical or healthcare type domains and which may process requests for such healthcare operations via the request processing pipeline 108 input as either structured or unstructured requests, natural language input questions, or the like.

In one illustrative embodiment, the cognitive system 100 is a healthcare cognitive system that provides decision support functionality for medical personnel, such as doctors, nurses, technicians, and the like, to assist them in making determinations as to how to treat a patient. In so doing, the cognitive system 100 is augmented, in accordance with the mechanisms of the illustrative embodiments, to include logic implemented in specialized hardware, specialized software executed on hardware, or any combination of specialized hardware and software executed on hardware, for implementing a patient EMR summarization engine 120 with deduplication of medical concepts present in the patient EMR data. The patient EMR summarization engine 120 with deduplication engine 130 may operate in conjunction with the cognitive system 100 to provide a patient EMR summary without duplicate patient information with regard to the same medical concepts, which may be provided in combination with other cognitive operations performed by the cognitive system 100. Alternatively, the patient EMR summarization engine 120 and deduplication engine 130 may operate as a separate system from that of the cognitive system 100 and may provide its operations independently, or with minimized use of logic of the cognitive system 100 to support functions of the patient EMR summarization engine 120 and deduplication engine 130, e.g., utilizing the parsing and natural language processing (NLP) mechanisms of the cognitive system 100 to provide functional support for parsing and identifying patient EMR elements in the patient EMR summarization engine 120 and deduplication engine 130.

Assuming an embodiment in which the cognitive system 100 operates in conjunction with the patient EMR summarization engine 120 with deduplication engine 130, the cognitive system 100 may receive a request to provide patient EMR information and/or perform other cognitive operations, such as providing a treatment recommendation, for example. In response to the request, patient EMR data is retrieved from the corpus 106, or another dedicated corpus of patient EMR data 150 which may be associated with the cognitive system 100 and/or accessible via the network 102, which may include patient EMR databases in which patient information for patients may be obtained from various sources and compiled into data structures which together constitute patient EMRs for the various patients. The request may specify the identity of the user requesting the cognitive operation and/or patient information presentation, as well as particular criteria for performing the cognitive operation and/or patient information presentation. For example, the request may specify that the user wishes to have a patient EMR summary focused on a particular clinical data category, e.g., problem list, medications, etc. The request may further specify the target of the operations, such as the name or identifier of the patient for which the cognitive operation and/or presentation of patient information is to be performed.

The patient EMR data for the identified patient may be retrieved by the cognitive system 100 from the corpus 106 and parsed by the cognitive system 100 to extract patient EMR elements, e.g., terms, phrases, medical codes, or other instances of medical concepts of interest. The cognitive system 100 may make use of one or more resource knowledge data structures, such as ontology data structures, knowledge bases of medical concepts, dictionary data structures, medical code scheme data structures defining the medical codes used to designate various medical concepts according to a particular scheme, and the like. Alternatively, the patient EMR summarization engine 120 may retrieve the patient EMR data and may further comprise parsing logic, and either comprise or have access to resource knowledge data structures, which may be used to perform the parsing and identification of patient EMR elements itself without the need to invoke the logic of the cognitive system 100 to perform such operations.

The retrieved patient EMR data for the patient specified in the request is received and parsed to extract al the terms, phrases, codes, etc., associated with a particular clinical data category, e.g., problem list, diagnosis, medications, symptoms, tests ordered, etc. specified in the request, if any. Otherwise, if no specific clinical data category is specified in the request, then a default set of clinical data categories or all clinical data categories supported by the implementation may be utilized. For example, the patient EMR data may be parsed to extract the problem list of the patient indicating all the medical problems associated with the patient. An example of a problem list that may be extracted from a patient EMR is shown in FIG. 1B, for example. As can be seen from FIG. 1B, the problem list comprises each term, phrase, medical code, etc., corresponding to medical problem that is found in the patient's EMR data and thus, is a listing of instances of medical problems in the patient EMR data which may include duplicate medical concepts. The terms, phrases, codes, etc., (collectively referred to as patient EMR elements) that are extracted may be determined by using established knowledge bases, ontologies, dictionary data structures, medical coding scheme data structures, and the like, (collectively referred to as resource knowledge data structures, that specify recognizable patient EMR elements.

Having generated a listing of the patient EMR elements 122 corresponding to the particular clinical data category, hereafter considered to be textual phrases in the patient EMR for purposes of illustration only, the deduplication engine 130 may operate on the listing to remove duplicate instances of the same medical concepts. For example, similarity metric engine 132 of the deduplication engine 130, for each pairing of phrases, may calculate a similarity metric which is utilized to judge the lexical and semantic similarity of the pair of phrases. In one illustrative embodiment, the similarity metric for a pair of phrases may be calculated as a pairwise similarity metric $s(d_i, d_j)$ where d is a phrase extracted from the patient EMR data, e.g., the phrases extracted from the patient EMR data may comprise N phrases $(d_1, d_2, \ldots, d_N)$ for a clinical data category C. The similarity metric $s(d_i, d_j)=1$ if $d_i$ and $d_j$ are semantically related phrases in a knowledge base, such as a knowledge base derived from UMLS, for example. The semantic relationship captured is of several types, e.g., same CUI, equivalent concepts, synonyms, related by generalization or specialization hierarchy in the ontology, by virtue of relation to other phrases, etc. Otherwise, if the phrases are not semantically related phrases, then $s(d_i, d_j)=lcf(d_i, d_j)$ which is the longest common subfix (lcf) match between the phrases $d_i$ and $d_j$ after pre-processing for ignore words, e.g., words that are adjectives such as severity adjectives, standard abbreviations, such as HCC (history of current complication), or other ignore words particular to the particular clinical data category.

The lexical and semantic similarity metrics are linearly combined and summed up to 1 for maximum value. With the similarity metric, a similarity of "1", for example, indicates that the phrases are lexically and semantically similar, and a similarity metric value less than "1" indicates a relatively lower level of similarity down to a value of "0" indicating no lexical or semantic similarity. There are various ways in which the similarity metric may be determined with the example presented above being only one possible way of calculating the similarity metric. As mentioned previously, the similarity metric may be evaluated by making an overlap determination to determine how much overlap there is between one phrase and the other in the pairing. Another approach to determining similarity between the two phrases in the pairing is to map ontological identifiers corresponding to the phrases as previously discussed above.

Those patient EMR elements, or phrases in the above examples, that are considered to be highly similar to one another based on the similarity metric value and a predetermined threshold, e.g., a similarity metric value of 0.75 or higher, are considered representative of repetitions or duplicate information in the patient EMR. A clustering engine 134 may provide a union-find connected component algorithm that is executed on the highly similar patient EMR elements, or phrases, to consolidate similar patient EMR elements (e.g., phrases) into a cluster based on the calculated similarity metrics between the pairings. Multiple clusters may be established for each group of highly similar pairings, where each cluster may correspond to a medical concept. Thus, for example, phrases that are similar to one another from both a lexical and semantic basis may be clustered with each other while other phrases may be present in other clusters or otherwise not included in a cluster.

Representative patient EMR element selection engine 136 may select a representative patient EMR element, or phrase in these examples, from each cluster to represent the cluster of duplicate instances of medical concepts in the patient EMR. For example, if the cluster includes phrases such as "high blood pressure", "high BP", and "hypertension", then a representative phrase of "hypertension" may be selected to represent all of these instances of duplicate medical concepts. Various ranking rules may be employed for selecting a representative patient EMR element, and these ranking rules may be dependent upon the particular clinical data category. The ranking rules may also be user customizable such that the particular ranking rules implemented for selection of a representative patient EMR element is specific to the user. User configuration data structures 138 may be established or learned over time where the user's preferences for patient EMR elements is stored. For example, based on the user's own specification, such as during a registration or configuration operation, settings for the types of representative patient EMR elements that the use prefers may be indicated and stored in the user's configuration data structure 138. For example, one user may want to select phrases that represent the most severe instance of a clinical data phrase, while another user may utilize a different ranking rule, such as shortest phrase to give the most generalization, a phrase that corresponds to the CUI with the highest node in an ontology traversed, etc. The highest node in the ontology represents the broadest classification of the concept. For example, aortic aneurysm may be classified higher up in the ontology as aneurysm->vascular disorder->circulatory system. A default ranking rule may be utilized to select a representative patient EMR element by analyzing the cluster to identify those patient EMR elements that are closest to the center point of the cluster, as well as analyze the patient EMR elements in the clusters for various characteristics, e.g., parts of speech, and utilize these criteria to select a patient EMR element having a desirable characteristics and which is closest to the center of the cluster.

The selected representative patient EMR elements may then be used to generate a deduplicated listing of medical concepts 140 which does not include the repetitious medical concept instances present in the original listing. To the contrary, the separate instances may be replaced with a single instance comprising the representative patient EMR element with characteristic information corresponding to each of the duplicate instances that were replaced. For example, timestamps, clinical data values, doctor notes, and the like, for each instance may be associated with a single instance of the representative patient EMR element, such that the separate instances may still be accessed via a drill-down interaction by the user, as discussed hereafter. The result is a deduplicated listing of medical concepts 140 with corresponding instance characteristics, which may then be used as a basis for generating a patient EMR summary.

The patient EMR summarization engine 120 may then generate a summary representation 124 of the patient EMR information via a graphical user interface based on the deduplicated listing of medical concepts 140 extracted from the patient EMR for the desired clinical data category or categories. The summary representation 124 may include the representative patient EMR elements, e.g., phrases, but with duplicate instances of patient EMR elements corresponding to similar medical concepts having been removed. Thus, rather than having three separate instances of "high blood pressure", "high BP", and "hypertension", the patient EMR summary 124 may simply indicate "hypertension" being associated with the patient. Other characteristics of the instances of the duplicate medical concepts may be associated with the same deduplicated entry in the summary representation. For example, a single instance of "hypertension" may be included in the summary with corresponding characteristics indicating timestamps when the patient was diagnosed with the medical concept, regardless of the particular terms/phrases/codes used to indicate the medical concept. Thus, for example, for "hypertension" there may be a first timestamp associated with the date that the note "high blood pressure" was included in the patient EMR, a second timestamp when "high BP" was noted, and a third timestamp when "hypertension" was noted. Other characteristics may also be included, such as any related clinical values, e.g., actual blood pressure readings, laboratory results, or the like.

The patient EMR summary graphical user interface may be output to the requestor's client computing device, e.g., client 110, for presentation to the user. The user may interact with the patient EMR summary graphical user interface to access the various patient EMR information in the summary view. Moreover, the user may access more detailed information from the summary view representation of the patient EMR data via a "drill-down" mechanism of the graphical user interface. That is, the user may access the representative patient EMR element and drill down into the individual characteristic information of the duplicate instances that were replaced by the representative patient EMR element, e.g., representative term, phrase, medical code, or the like. Thus, while a patient EMR summary representation 124 is provided for ease of use by the user and browsing, the details of the individual instances are not lost and may be accessed via the graphical user interface should the user determine that such details are needed to perform decision making operations.

The process described above may be performed with regard to a plurality of different clinical data categories. The patient information in the patient EMR for each of these clinical data categories may be deduplicated using the mechanisms of the illustrative embodiments so as to eliminate duplicated instances of the same medical concepts present within the patient EMR data. The resulting deduplicated patient information may together be compiled into the summary representation of the patient EMR data which is more concise and able to be browsed by the medical professional to obtain a quick and clear representation of the medical condition of the patient. The summary representation is presented in a graphical user interface such that the medical professional may be able to access the underlying detailed information corresponding to the summary representation.

Thus, the illustrative embodiments provide mechanisms for performing deduplication of medical concepts in patient electronic medical records when generating a summary representation of the patient electronic medical record. With the illustrative embodiments, the lexical and semantic similarity is combined to identify a set of related patient EMR elements, e.g., phrases, terms, medical codes, etc. in a patient EMR element list of a clinical category, such as problem lists, diagnosis, medications, symptoms, tests ordered, etc. A similarity metric is utilized to judge the lexical and semantic similarity of candidate phrases, medical codes, terms, etc., and a connected component algorithm is used to consolidate these phrases, terms, codes, etc., into a cluster. A representative element, e.g., phrase, term, code, or the like, is selected from the cluster as a deduplicated element of the relevant medical concept for use in generating a summary representation of a patient's electronic medical record. The resulting summary is more usable by medical personnel and easier to browse, allowing the medical personnel to obtain a necessary information for providing decision support more quickly and efficiently.

As is evident from the above, the mechanisms of the illustrative embodiments are rooted in the computer technology arts and are implemented using logic present in such computing or data processing systems. These computing or data processing systems are specifically configured, either through hardware, software, or a combination of hardware and software, to implement the various operations described above. Thus, having been configured to perform these specific operations, the resulting configured computing or data processing systems are not generic computing or data processing systems simply performing generic computing operations or functions. To the contrary, the specifically configured computing devices or data processing systems are specific non-generic computing devices or data processing systems. As such, FIG. 2 is provided as an example of one type of data processing system in which aspects of the present invention may be implemented through specific configuration of the data processing system via the loading of software into memory and execution of that particular software on one or more processors of the data processing system to perform the described operations. Many other types of data processing systems may be likewise configured to specifically implement the mechanisms of the illustrative embodiments.

FIG. 2 is a block diagram of an example data processing system in which aspects of the illustrative embodiments are implemented. Data processing system 200 is an example of a computer, such as server 104 or client 110 in FIG. 1, in which computer usable code or instructions implementing the processes for illustrative embodiments of the present invention are located. In one illustrative embodiment, FIG. 2 represents a server computing device, such as a server 104, which, which implements a cognitive system 100 and QA system pipeline 108 augmented to include the additional mechanisms of the illustrative embodiments described hereafter.

In the depicted example, data processing system 200 employs a hub architecture including North Bridge and Memory Controller Hub (NB/MCH) 202 and South Bridge and Input/Output (I/O) Controller Hub (SB/ICH) 204. Processing unit 206, main memory 208, and graphics processor 210 are connected to NB/MCH 202. Graphics processor 210 is connected to NB/MCH 202 through an accelerated graphics port (AGP).

In the depicted example, local area network (LAN) adapter 212 connects to SB/ICH 204. Audio adapter 216, keyboard and mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SB/ICH 204 through bus 238 and bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS).

HDD 226 and CD-ROM drive 230 connect to SB/ICH 204 through bus 240. HDD 226 and CD-ROM drive 230 may use, for example, an integrated drive electronics (IDE) or serial advanced technology attachment (SATA) interface. Super I/O (SIO) device 236 is connected to SB/ICH 204.

An operating system runs on processing unit 206. The operating system coordinates and provides control of various components within the data processing system 200 in FIG. 2. As a client, the operating system is a commercially available operating system such as Microsoft® Windows 10°. An object-oriented programming system, such as the Java™ programming system, may run in conjunction with the operating system and provides calls to the operating system from Java™ programs or applications executing on data processing system 200.

As a server, data processing system 200 may be, for example, an IBM® eServer™ System p® computer system, running the Advanced Interactive Executive) (AIX®) operating system or the LINUX® operating system. Data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and are loaded into main memory 208 for execution by processing unit 206. The processes for illustrative embodiments of the present invention are performed by processing unit 206 using computer usable program code, which is located in a memory such as, for example, main memory 208, ROM 224, or in one or more peripheral devices 226 and 230, for example.

A bus system, such as bus 238 or bus 240 as shown in FIG. 2, is comprised of one or more buses. Of course, the bus system may be implemented using any type of communication fabric or architecture that provides for a transfer of data between different components or devices attached to the fabric or architecture. A communication unit, such as modem 222 or network adapter 212 of FIG. 2, includes one or more devices used to transmit and receive data. A memory may be, for example, main memory 208, ROM 224, or a cache such as found in NB/MCH 202 in FIG. 2.

Those of ordinary skill in the art will appreciate that the hardware depicted in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the SMP system mentioned previously, without departing from the spirit and scope of the present invention.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation.

FIG. 3 is an example diagram illustrating an interaction of elements of a healthcare cognitive system in accordance with one illustrative embodiment. The example diagram of FIG. 3 depicts an implementation of a healthcare cognitive system 300 that is configured to provide medical treatment recommendations for patients. As part of providing medical treatment recommendations for patients, the healthcare cognitive system 300 may further provide patient EMR summary representations with deduplication in accordance with one or more of the illustrative embodiments. For example, such summary representations may be used as a further evidential basis for supporting the medical treatment recommendations generated by the cognitive system and may be presented to a medical professional for viewing and browsing when considering the medical treatment recommendations, for example. However, it should be appreciated that this is only an example implementation and other healthcare operations may be implemented in other embodiments of the healthcare cognitive system 300 without departing from the spirit and scope of the present invention.

Moreover, it should be appreciated that while FIG. 3 depicts the patient 302 and user 306 as human figures, the interactions with and between these entities may be performed using computing devices, medical equipment, and/or the like, such that entities 302 and 306 may in fact be computing devices, e.g., client computing devices. For example, the interactions 304, 314, 316, and 330 between the patient 302 and the user 306 may be performed orally, e.g., a doctor interviewing a patient, and may involve the use of one or more medical instruments, monitoring devices, or the like, to collect information that may be input to the healthcare cognitive system 300 as patient attributes 318. Interactions between the user 306 and the healthcare cognitive system 300 will be electronic via a user computing device (not shown), such as a client computing device 110 or 112 in FIG. 1A, communicating with the healthcare cognitive system 300 via one or more data communication links and potentially one or more data networks.

As shown in FIG. 3, in accordance with one illustrative embodiment, a patient 302 presents symptoms 304 of a medical malady or condition to a user 306, such as a healthcare practitioner, technician, or the like. The user 306 may interact with the patient 302 via a question 314 and response 316 exchange where the user gathers more information about the patient 302, the symptoms 304, and the medical malady or condition of the patient 302. It should be appreciated that the questions/responses may in fact also represent the user 306 gathering information from the patient 302 using various medical equipment, e.g., blood pressure monitors, thermometers, wearable health and activity monitoring devices associated with the patient such as a FitBit™, a wearable heart monitor, or any other medical equipment that may monitor one or more medical characteristics of the patient 302. In some cases such medical equipment may be medical equipment typically used in hospitals or medical centers to monitor vital signs and medical conditions of patients that are present in hospital beds for observation or medical treatment.

In response, the user 302 submits a request 308 to the healthcare cognitive system 300, such as via a user interface on a client computing device that is configured to allow users to submit requests to the healthcare cognitive system 300 in a format that the healthcare cognitive system 300 can parse and process. The request 308 may include, or be accompanied with, information identifying patient attributes 318. These patient attributes 318 may include, for example, an identifier of the patient 302 from which patient EMRs 322 for the patient may be retrieved, demographic information about the patient, the symptoms 304, and other pertinent information obtained from the responses 316 to the questions 314 or information obtained from medical equipment used to monitor or gather data about the condition of the patient 302. Any information about the patient 302 that may be relevant to a cognitive evaluation of the patient by the healthcare cognitive system 300 may be included in the request 308 and/or patient attributes 318 and which may be used to generate a patient EMR summary representation with deduplication of instances of medical concepts with regard to one or more of the illustrative embodiments.

The healthcare cognitive system 300 provides a cognitive system that is specifically configured to perform an implementation specific healthcare oriented cognitive operation. In the depicted example, this healthcare oriented cognitive operation is directed to providing a treatment recommendation 328 to the user 306 to assist the user 306 in treating the patient 302 based on their reported symptoms 304 and other information gathered about the patient 302 via the question 314 and response 316 process and/or medical equipment monitoring/data gathering. The healthcare cognitive system 300 operates on the request 308 and patient attributes 318 utilizing information gathered from the medical corpus and other source data 326, treatment guidance data 324, and the patient EMRs 322 associated with the patient 302 to generate one or more treatment recommendation 328. The treatment recommendations 328 may be presented in a ranked ordering with associated supporting evidence, obtained from the patient attributes 318 and data sources 322-326, indicating the reasoning as to why the treatment recommendation 328 is being provided and why it is ranked in the manner that it is ranked.

For example, based on the request 308 and the patient attributes 318, the healthcare cognitive system 300 may operate on the request, such as by using a QA pipeline type processing as described herein, to parse the request 308 and patient attributes 318 to determine what is being requested and the criteria upon which the request is to be generated as identified by the patient attributes 318, and may perform various operations for generating queries that are sent to the data sources 322-326 to retrieve data, generate candidate treatment recommendations (or answers to the input question), and score these candidate treatment recommendations based on supporting evidence found in the data sources 322-326. In the depicted example, the patient EMRs 322 is a patient information repository that collects patient data from a variety of sources, e.g., hospitals, laboratories, physicians' offices, health insurance companies, pharmacies, etc. The patient EMRs 322 store various information about individual patients, such as patient 302, in a manner (structured, unstructured, or a mix of structured and unstructured formats) that the information may be retrieved and processed by the healthcare cognitive system 300. This patient information may comprise various demographic information about patients, personal contact information about patients, employment information, health insurance information, laboratory reports, physician reports from office visits, hospital charts, historical information regarding previous diagnoses, symptoms, treatments, prescription information, etc. Based on an identifier of the patient 302, the patient's corresponding EMRs 322 from this patient repository may be retrieved by the healthcare cognitive system 300 and searched/processed to generate treatment recommendations 328.

The treatment guidance data 324 provides a knowledge base of medical knowledge that is used to identify potential treatments for a patient based on the patient's attributes 318 and historical information presented in the patient's EMRs 322. This treatment guidance data 324 may be obtained from official treatment guidelines and policies issued by medical authorities, e.g., the American Medical Association, may be obtained from widely accepted physician medical and reference texts, e.g., the Physician's Desk Reference, insurance company guidelines, or the like. The treatment guidance data 324 may be provided in any suitable form that may be ingested by the healthcare cognitive system 300 including both structured and unstructured formats.

In some cases, such treatment guidance data 324 may be provided in the form of rules that indicate the criteria required to be present, and/or required not to be present, for the corresponding treatment to be applicable to a particular patient for treating a particular symptom or medical malady/condition. For example, the treatment guidance data 324 may comprise a treatment recommendation rule that indicates that for a treatment of Decitabine, strict criteria for the use of such a treatment is that the patient 302 is less than or equal to 60 years of age, has acute myeloid leukemia (AML), and no evidence of cardiac disease. Thus, for a patient 302 that is 59 years of age, has AML, and does not have any evidence in their patient attributes 318 or patient EMRs indicating evidence of cardiac disease, the following conditions of the treatment rule exist:

Age <=60 years=59 (MET);
Patient has AML=AML (MET); and
Cardiac Disease=false (MET)

Since all of the criteria of the treatment rule are met by the specific information about this patient 302, then the treatment of Decitabine is a candidate treatment for consideration for this patient 302. However, if the patient had been 69 years old, the first criterion would not have been met and the Decitabine treatment would not be a candidate treatment for consideration for this patient 302. Various potential treatment recommendations may be evaluated by the healthcare cognitive system 300 based on ingested treatment guidance data 324 to identify subsets of candidate treatments for further consideration by the healthcare cognitive system 300 by scoring such candidate treatments based on evidential data obtained from the patient EMRs 322 and medical corpus and other source data 326.

For example, data mining processes may be employed to mine the data in sources 322 and 326 to identify evidential data supporting and/or refuting the applicability of the candidate treatments to the particular patient 302 as characterized by the patient's patient attributes 318 and EMRs 322. For example, for each of the criteria of the treatment rule, the results of the data mining provides a set of evidence that supports giving the treatment in the cases where the criterion is "MET" and in cases where the criterion is "NOT MET." The healthcare cognitive system 300 processes the evidence in accordance with various cognitive logic algorithms to generate a confidence score for each candidate treatment recommendation indicating a confidence that the corresponding candidate treatment recommendation is valid for the patient 302. The candidate treatment recommendations may then be ranked according to their confidence scores and presented to the user 306 as a ranked listing of treatment recommendations 328. In some cases, only a highest ranked, or final answer, is returned as the treatment recommendation 328. The treatment recommendation 328 may be presented to the user 306 in a manner that the underlying evidence evaluated by the healthcare cognitive system 300 may be accessible, such as via a drilldown interface, so that the user 306 may identify the reasons why the treatment recommendation 328 is being provided by the healthcare cognitive system 300.

In accordance with the illustrative embodiments herein, the healthcare cognitive system 300 is augmented to include a patient EMR summarization engine 120 and deduplication engine 130, as previously described above with regard to FIG. 1A. The patient EMR summarization engine 120 provides the functionality previously described to generate a summary representation of the patient's EMR data for ease of use and browsing by the user 306. The deduplication engine 130 provides functionality for removing duplicate instances of medical concepts within a patient EMR element listing extracted from the patient's EMR data and compiling characteristic information for the duplicate instances for association with a representative EMR element selected to represent the duplicate instances. The patient EMR summarization engine 120 generates the summary representation based on the deduplicated listing of the instances of the medical concepts extracted from the patient EMR data for the patient, and for any selected clinical data categories. The summary representation may be provided to the user 306 for viewing, browsing, and the like. The user 306 may drill-down into the summary representation to access the detailed characteristic information for instances of the medical concept represented by the selected representative patient EMR element. The providing of the summary representation may be provided as supportive data for supporting decision making by the user 306 as well as evidential data for supporting treatment recommendations generated by the healthcare cognitive system.

While FIG. 3 is depicted with an interaction between the patient 302 and a user 306, which may be a healthcare practitioner such as a physician, nurse, physician's assistant, lab technician, or any other healthcare worker, for example, the illustrative embodiments do not require such. Rather, the patient 302 may interact directly with the healthcare cognitive system 300 without having to go through an interaction with the user 306 and the user 306 may interact with the healthcare cognitive system 300 without having to interact with the patient 302. For example, in the first case, the patient 302 may be requesting 308 treatment recommendations 328 from the healthcare cognitive system 300 directly based on the symptoms 304 provided by the patient 302 to the healthcare cognitive system 300. Moreover, the healthcare cognitive system 300 may actually have logic for automatically posing questions 314 to the patient 302 and receiving responses 316 from the patient 302 to assist with data collection for generating treatment recommendations 328. In the latter case, the user 306 may operate based on only information previously gathered and present in the patient EMR 322 by sending a request 308 along with patient attributes 318 and obtaining treatment recommendations in response from the healthcare cognitive system 300. Thus, the depiction in FIG. 3 is only an example and should not be interpreted as requiring the particular interactions depicted when many modifications may be made without departing from the spirit and scope of the present invention. It should be appreciated, however, that at no time should the treatment itself be administered to the patient 302 without prior approval of the healthcare professional treating the patient, i.e. final determinations as to treatments given to a patient will always fall on the healthcare professional with the mechanisms of the illustrative embodiments serving only as an advisory tool for the healthcare professional (user 306) and/or patient 302.

Figure 4:
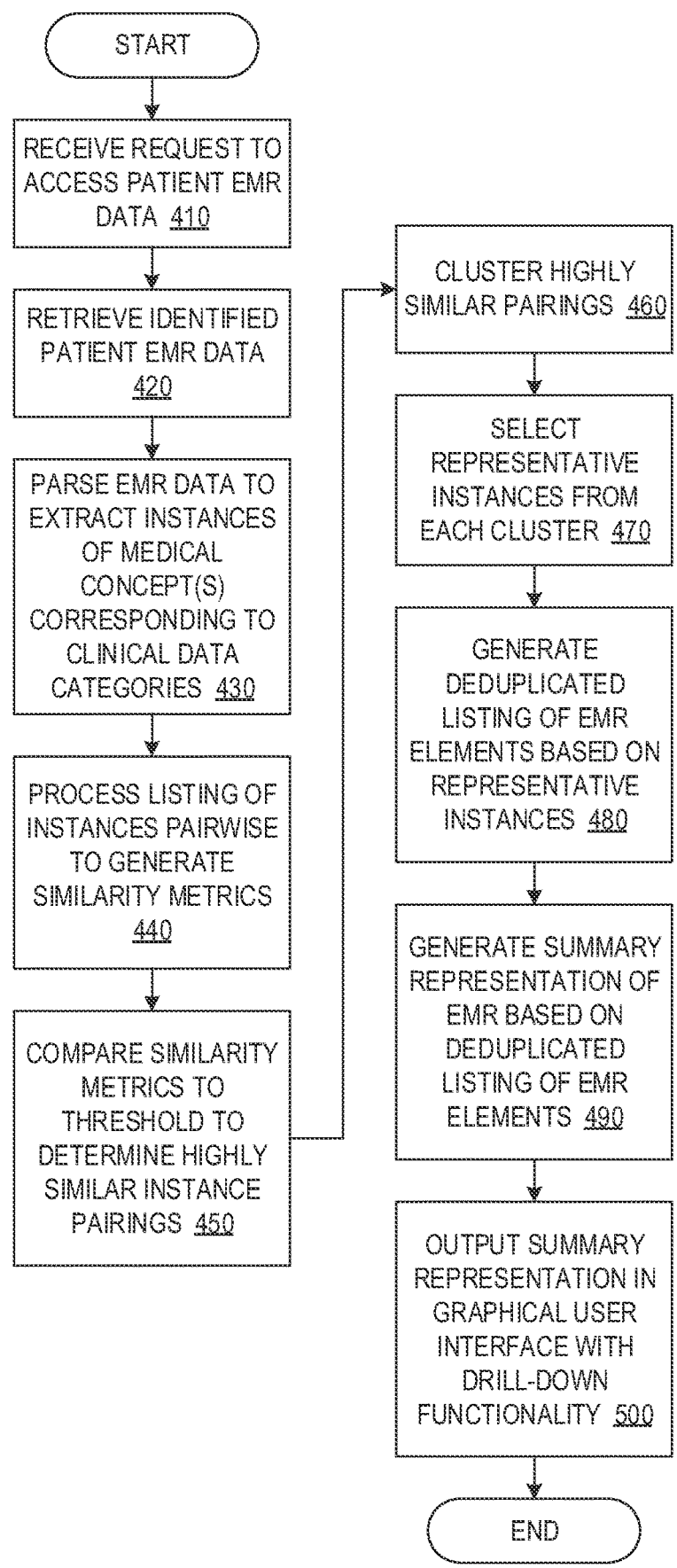
FIG. 4 is a flowchart outlining an example operation for generating a patient EMR summary representation with deduplication of instances of medical concepts extracted from the patient EMR data.

FIG. 4 is a flowchart outlining an example operation for generating a patient EMR summary representation with deduplication of instances of medical concepts extracted from the patient EMR data. As shown in FIG. 4, the operation starts by receiving a request to access patient EMR data (step 410) where the request may specify a user requesting the access, the patient for which patient EMR data is to be retrieved, and any clinical data categories that are of particular interest to the user submitting the request. The patient EMR data corresponding to the identified patient is retrieved (step 420) and parsed with regard to any specified clinical data categories, or a default setting of clinical data categories, to extract instances of medical concepts corresponding to the clinical data categories from the patient EMR data (step 430). The resulting listing of instances of medical concepts is then processed pairwise to generate similarity metrics between each of the pairs of instances in the listing (step 440).

The similarity metrics for the pairings are compared to one or more thresholds to determine those pairings that are highly similar (step 450). The highly similar pairings are clustered into one or more clusters, where each cluster comprises instances of a same medical concept (step 460). For each cluster, a representative patient EMR element is selected (step 470). The representative patient EMR element may be selected in accordance with a set of ranking rules, where these ranking rules may be specific to the particular user that requested the access to the patient EMR data. The representative patient EMR element is then used, along with other representative patient EMR elements for other clusters, to generate a deduplicated listing of instances of medical concepts (step 480).

The deduplicated listing of medical concepts is used to generate a summary representation of the patient EMR data (step 490) as a graphical user interface with drill-down functionality. The summary representation is output to the requestor computing device as a graphical user interface through which a user may interact to view and browse patient EMR data information in a user friendly manner (step 500). The operation then ends.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising a processor and a memory, the memory comprising instructions that are executed by the processor to configure the processor to implement a patient summary generation engine, the method comprising the patient summary generation engine:
    configuring computer natural language processing logic to extract instances of a medical concept from patient electronic medical records (EMRs) based on portions of content corresponding to terms, phrases, or medical codes of a clinical data category specific knowledge resource data structure;
    performing a similarity analysis between a plurality of combinations of the instances of the medical concept in a patient (EMR) to thereby calculate, for each combination of instances in the plurality of combinations of instances of the medical concept, a similarity metric value, wherein at least two of the instances are different representations of the medical concept;
    clustering the instances of the medical concept based on the calculated similarity metric values for each combination in the plurality of combinations of the instances of the medical concept to thereby generate one or more clusters; and
    generating a summary output of the patient EMR based on the one or more clusters of the instances of the medical concept at least by selecting a representative instance of the medical concept from each cluster in the one or more clusters for inclusion in the summary output.

2. The method of claim 1, wherein the different representations comprise at least one of different terms referring to the same medical concept, different phrases referring to the same medical concept, or different medical codes referring to the same medical concept.

3. The method of claim 1, further comprising:
    receiving a request to generate the summary output of the patient EMR, wherein the request includes an identifier corresponding to the patient EMR and an identifier of at least one clinical data category, and wherein the medical concept is associated with the clinical data category specified in the request.

4. The method of claim 3, wherein the patient EMR is parsed to identify instances of the medical concept associated with the clinical data category based on a predefined knowledge resource data structure corresponding to the clinical data category.

5. The method of claim 3, wherein selecting the representative instance of the medical concept from each cluster in the one or more clusters comprises applying user specific ranking rules for ranking instances of the medical concept in the one or more clusters and selecting an instance of the medical concept for each cluster based on the relative ranking of the instances of the medical concept, wherein the user specific ranking rules are specific to a user who submitted the request.

6. The method of claim 5, wherein the user specific ranking rule specifies higher rankings for a shortest clinical data phrase in the cluster, a clinical data phrase that corresponds to a concept unique identifier with a highest node in an ontology, or a most severe instance of a clinical data phrase.

7. The method of claim 1, wherein performing the similarity analysis between each of the instances of the medical concept comprises performing, for each pair of instances of the medical concept, a combined lexical and semantic similarity analysis to determine a corresponding similarity metric value for the pair of instances of the medical concept.

8. The method of claim 7, wherein performing the similarity analysis between each of the instances of the medical concept comprises determining, for each pair of instances of medical concepts, at least one of a degree of overlap of text corresponding to the instances of medical concepts in the pair, or determining a mapping between ontological identifiers corresponding to the instances of medical concepts in the pair.

9. The method of claim 7, wherein performing the similarity analysis between each of the instances of the medical concept further comprises, for each pair of instances of the medical concept, a corresponding similarity metric value to a threshold similarity metric value, wherein the clustering is performed on pairs of instances of the medical concept whose corresponding similarity metric value is equal to or greater than the threshold similarity metric value.

10. The method of claim 7, wherein performing the similarity analysis between each of the instances of the medical concept further comprises performing a context based filtering of the instances of medical concepts to remove terms or phrases that do not identify the medical concept.

11. A computer program product comprising a non-transitory computer readable medium having a computer readable program stored therein, wherein the computer readable program, when executed on a computing device, causes the computing device to implement a patient summary generation engine which operates to:
configure computer natural language processing logic to extract instances of a medical concept from patient electronic medical records (EMRs) based on portions of content corresponding to terms, phrases, or medical codes of a clinical data category specific knowledge resource data structure;
perform a similarity analysis between a plurality of combinations of the instances of the medical concept in a patient EMR to thereby calculate, for each combination of instances in the plurality of combinations of instances of the medical concept, a similarity metric value, wherein at least two of the instances are different representations of the medical concept;
cluster the instances of the medical concept based on the calculated similarity metric values for each combination in the plurality of combinations of the instances of the medical concept to thereby generate one or more clusters; and
generate a summary output of the patient EMR based on the one or more clusters of the instances of the medical concept at least by selecting a representative instance of the medical concept from each cluster in the one or more clusters for inclusion in the summary output.

12. The computer program product of claim 11, wherein the different representations comprise at least one of different terms referring to the same medical concept, different phrases referring to the same medical concept, or different medical codes referring to the same medical concept.

13. The computer program product of claim 11, further comprising:
receiving a request to generate the summary output of the patient EMR, wherein the request includes an identifier corresponding to the patient EMR and an identifier of at least one clinical data category, and wherein the medical concept is associated with the clinical data category specified in the request.

14. The computer program product of claim 13, wherein the patient EMR is parsed to identify instances of the medical concept associated with the clinical data category based on a predefined knowledge resource data structure corresponding to the clinical data category.

15. The computer program product of claim 13, wherein selecting the representative instance of the medical concept from each cluster in the one or more clusters comprises applying user specific ranking rules for ranking instances of the medical concept in the one or more clusters and selecting an instance of the medical concept for each cluster based on the relative ranking of the instances of the medical concept, wherein the user specific ranking rules are specific to a user who submitted the request.

16. The computer program product of claim 11, wherein performing the similarity analysis between each of the instances of the medical concept comprises performing, for each pair of instances of the medical concept, a combined lexical and semantic similarity analysis to determine a corresponding similarity metric value for the pair of instances of the medical concept.

17. The computer program product of claim 16, wherein performing the similarity analysis between each of the instances of the medical concept comprises determining, for each pair of instances of medical concepts, at least one of a degree of overlap of text corresponding to the instances of medical concepts in the pair, or determining a mapping between ontological identifiers corresponding to the instances of medical concepts in the pair.

18. The computer program product of claim 16, wherein performing the similarity analysis between each of the instances of the medical concept further comprises, for each pair of instances of the medical concept, a corresponding similarity metric value to a threshold similarity metric value, wherein the clustering is performed on pairs of instances of the medical concept whose corresponding similarity metric value is equal to or greater than the threshold similarity metric value.

19. The computer program product of claim 16, wherein performing the similarity analysis between each of the instances of the medical concept further comprises performing a context based filtering of the instances of medical concepts to remove terms or phrases that do not identify the medical concept.

20. An apparatus comprising:
a processor; and
a memory coupled to the processor, wherein the memory comprises instructions which, when executed by the processor, cause the processor to implement a patient summary generation engine which operates to:
configure computer natural language processing logic to extract instances of a medical concept from patient electronic medical records (EMRs) based on portions of content corresponding to terms, phrases, or medical codes of a clinical data category specific knowledge resource data structure;

perform a similarity analysis between a plurality of combinations of the instances of the medical concept in a patient EMR to thereby calculate, for each combination of instances in the plurality of combinations of instances of the medical concept, a similarity metric value, wherein at least two of the instances are different representations of the medical concept;

cluster the instances of the medical concept based on the calculated similarity metric values for each combination in the plurality of combinations of the instances of the medical concept to thereby generate one or more clusters; and generate a summary output of the patient EMR based on the one or more clusters of the instances of the medical concept at least by selecting a representative instance of the medical concept from each cluster in the one or more clusters for inclusion in the summary output.

* * * * *